(12) United States Patent
Goldwasser

(10) Patent No.: US 6,183,847 B1
(45) Date of Patent: Feb. 6, 2001

(54) COATING SELECTIVE ZONES OF THIN WEBS TO CHANGE THE PERVIOUS CHARACTER THEREOF

(75) Inventor: Moshe Goldwasser, Tel Aviv (IL)

(73) Assignee: Avgol Ltd., Nonwoven Industries, Holon (IL)

(*) Notice: Under 35 U.S.C. 154(b), the term of this patent shall be extended for 0 days.

(21) Appl. No.: 09/182,665

(22) Filed: Oct. 30, 1998

Related U.S. Application Data

(60) Continuation-in-part of application No. 08/901,674, filed on Jul. 28, 1997, now Pat. No. 5,885,656, which is a division of application No. 08/434,672, filed on May 5, 1995, now Pat. No. 5,709,747, which is a continuation-in-part of application No. 08/232,692, filed on Apr. 25, 1994, now abandoned.

(51) Int. Cl.$^7$ ..................................................... B32B 27/02
(52) U.S. Cl. ........................... 428/219; 428/195; 428/224; 442/392; 442/400; 442/401; 427/288
(58) Field of Search ..................................... 428/175, 219, 428/224; 442/392, 400, 401; 427/288

(56) References Cited

U.S. PATENT DOCUMENTS 5,492,751  2/1996  Butt, Sr. et al. .
5,562,650 * 10/1996  Everett et al. ........................ 604/378

* cited by examiner

*Primary Examiner*—Terrel Morris
*Assistant Examiner*—Arti R. Singh
(74) *Attorney, Agent, or Firm*—Breiner & Breiner

(57) ABSTRACT

The process and apparatus of the present invention involves treating a well-integrated woven or non-woven web of hydrophobic fibers to make selected areas hydrophilic. It also can be used to make a web of hydrophilic fibers selectively hydrophobic. It uses a plurality of selectively adjustable covers on an applicator roll rotating in a bath of liquid to place the liquid material on selected areas of the web as the web moves over the roll. In a preferred embodiment the web is non-woven and the fibers are hydrophobic in nature, e.g., dry-laid or melt-blown polypropylene or polyethylene fibers or spun-bonded hydrophobic filaments. A woven web made of cotton or other hydrophilic fibers may also be used if the end result is to create partially hydrophobic areas on a hydrophilic web. The areas of liquid are positioned on the web only where desired so as to eliminate the excessive cost of unwanted and unnecessary coating material. If the web is hydrophobic, the liquid makes that area hydrophilic. If the web is hydrophilic, the liquid makes that area hydrophobic. Enhanced liquid containment and transport is obtained when at least one discontinuous fine fiber layer is utilized in the web and the fine fiber layer has a melt-blown content greater than zero but less than 1.5 gsm.

13 Claims, 3 Drawing Sheets

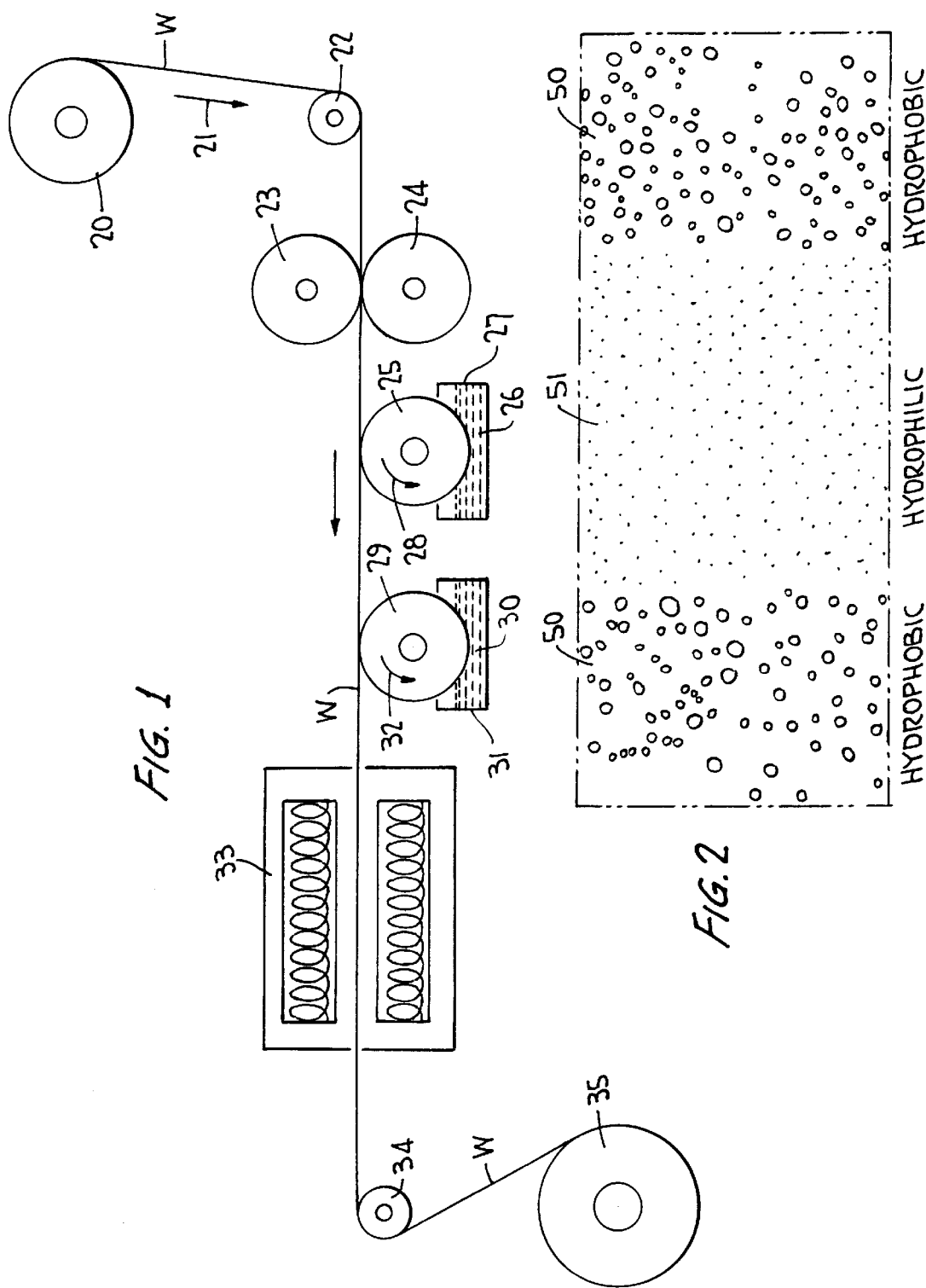

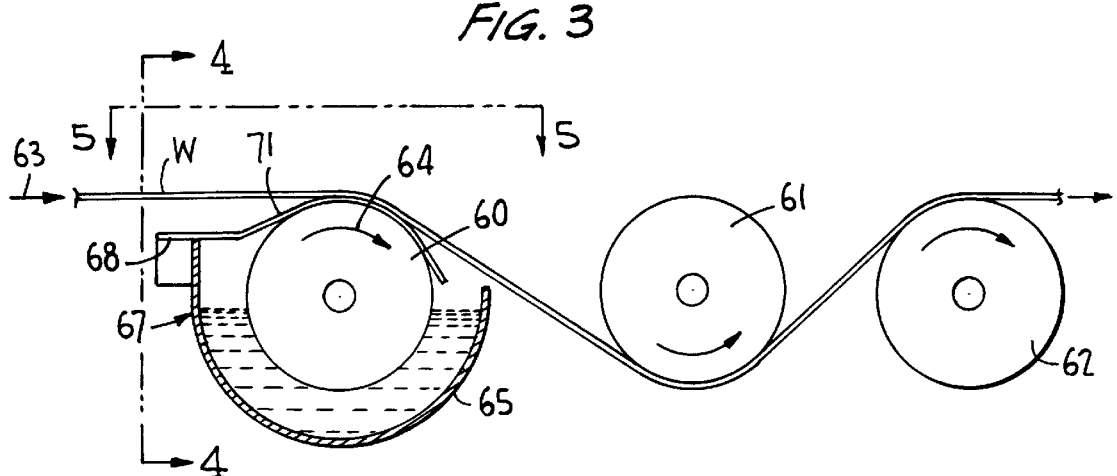
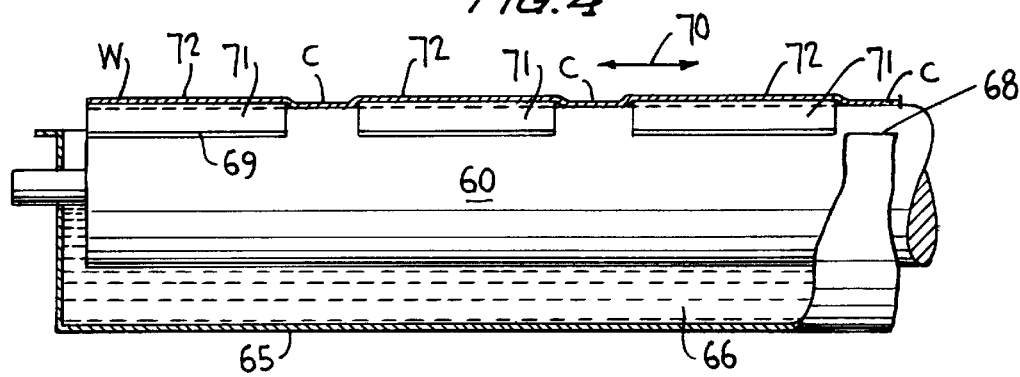
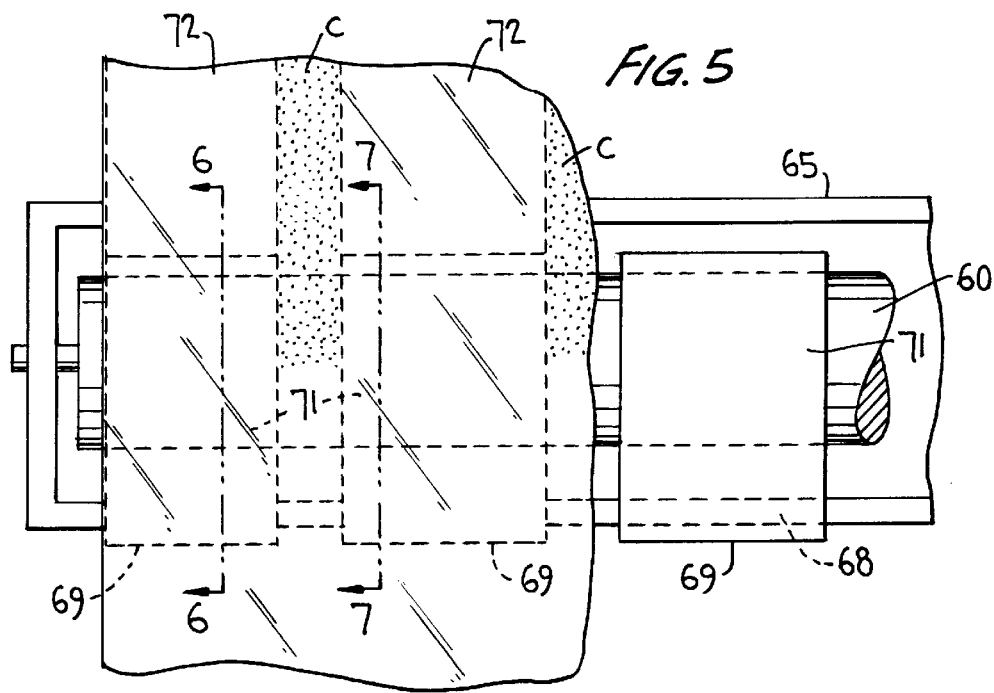

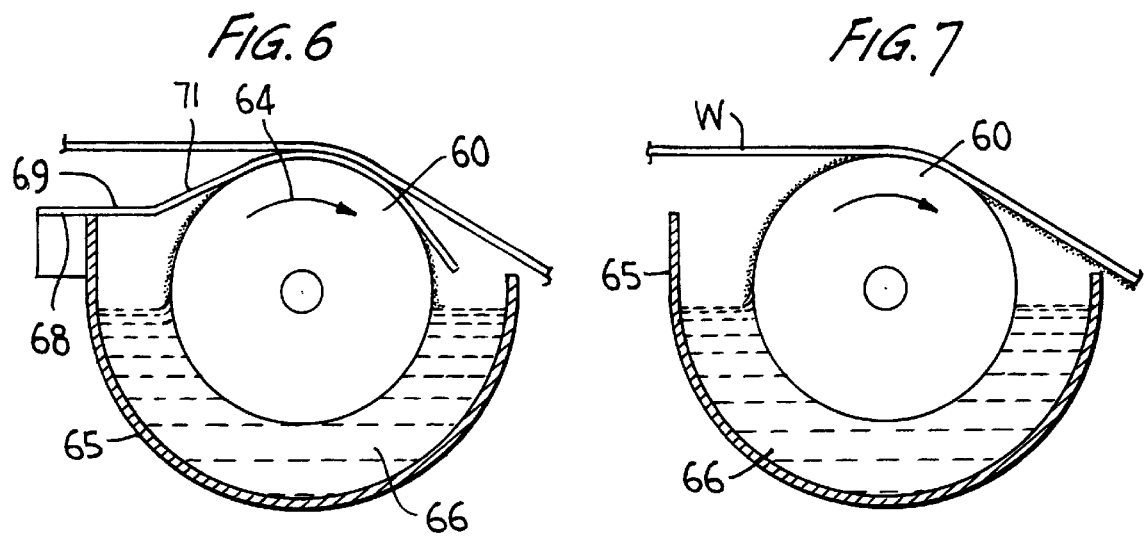
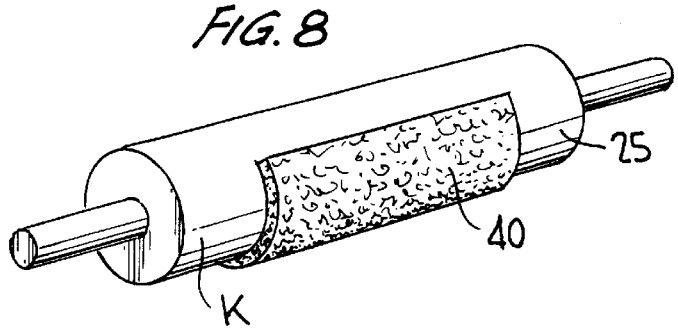
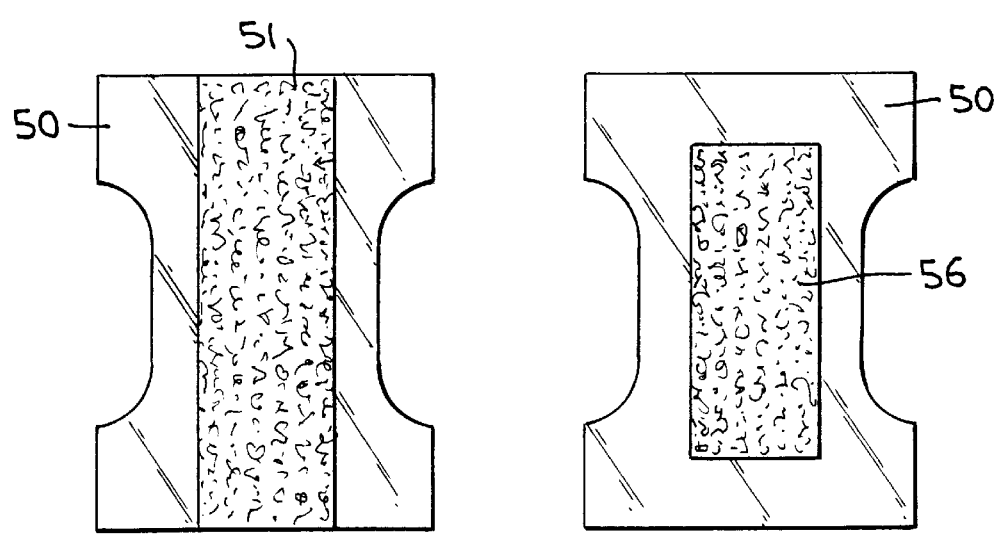

COATING SELECTIVE ZONES OF THIN WEBS TO CHANGE THE PERVIOUS CHARACTER THEREOF

RELATED APPLICATIONS

This is a continuation-in-part application of U.S. Ser. No. 08/901,674 filed Jul. 28, 1997, now U.S. Pat. No. 5,885,656, which is a division of U.S. Ser. No. 08/434,672 filed May 5, 1995, now U.S. Pat. No. 5,709,747, which in turn is a continuation-in-part application of Ser. No. 08/232,692 filed Apr. 25, 1994, now abandoned.

BACKGROUND OF THE INVENTION

It is well-known in the art of manufacturing disposable baby diapers or other sanitary disposable absorbent products such as sanitary napkins, adult incontinence pads, and hospital bed pads to provide a structure wherein the coversheet or coverstock or top sheet (i.e., that portion of the product which is in contact with a person's skin) is made of a hydrophilic material so as to be pervious to liquids, such as urine. This permits the ready pass-through of the liquid into the absorbent core or pad which lies beneath the coverstock. In the past, some coverstocks have also been made of cotton, blends of cotton and rayon, or blends of rayon with a bondinq fiber such as polyethylene.

Such coverstock, however, has been undesirable because it tends to retain the moisture and, thus, feel wet to the touch. Further, since the coverstock keeps the skin wet, it is more likely to cause a skin rash, diaper rash, or the like.

Therefore, in more recent years, it has been found desirable to use a coverstock made of hydrophobic fibers or filaments, such as polypropylene or polyester, either carded, spun-bonded, melt-blown, or the like. However, since hydrophobic material inherently tends to interfere with the pass-through of urine into the absorbent pad, it has been found necessary to treat the web with a hydrophilic-inducing material, e.g., a surfactant such as Triton X-102 distributed by Rohm & Haas Co. of Philadelphia, Pa., or MAGNA-SOFT manufactured by the Union Carbide Company.

The surfactant usually is incorporated with the fibers by the fiber manufacturers before being sent to the web manufacturer who forms a web which is substantially uniformly hydrophilic. A web thus formed when used as the top sheet in a baby or adult diaper is then coated in areas where perviousness is not only unnecessary but also undesirable. In a more recent form of diaper construction, a strip of non-woven web of hydrophilic material is assembled side-by-side between two strips or webs of hydrophobic fibers. When such a 3-strip web is placed upon a diaper, with the pervious strip in the longitudinal center of the diaper, the urine can pass to the absorbent core through the center strip but not along the sides where the coverstock is impervious. However, such a pre-formed web assembled from three different materials is costly to make and more difficult to run on a diaper machine because of the seam-lines between the hydrophilic and hydrophobic strips.

Further, as described in U.S. Pat. No. 5,492,751, when non-woven laminates are made in a conventional manner, the fine fiber layer(s) (melt blown layer) has a basis weight of at least about 1.5 to 26 grams per square meter (gsm) and the continuous filament layer(s) has a basis weight of from about 5–30 gsm in order to achieve the desired softness and breathability in the laminate. Thus, the laminate would be more desirable if it were lighter weight while still having the desirable hydrophilic and hydrophobic properties. Additionally, cost benefits would be achievable in manufacture due to the need for lesser amounts of material in manufacture.

In order to overcome the above deficiencies, this invention provides a process for applying a coating material to a one-piece hydrophobic web only where the coating is desired.

Such a process is different from a padding process which applies a liquid, such as an adhesive, to an unbonded web of fibers (to create an integrated nonwoven web).

The prior art fails to teach the unique process of the present invention to produce a one-piece web with precisely located coating zones, in particular including a fine fiber layer with a melt blown content less than 1.5 gsm.

OBJECTS OF THE INVENTION

Thus, one primary object of the present invention is to provide a process and apparatus for the application of surfactant substances to a web of nonwoven hydrophobic material so as to make selected areas of the web hydrophilic.

Another primary object is to provide a process and apparatus for applying hydrophobic-inducing materials to selected areas of a web of hydrophilic material so as to render the selected areas impervious to the passage of liquids.

Another primary object is to provide a one-piece web which has selected liquid-pervious areas for the coverstock of sanitary, disposable absorbent products.

Another primary object is to provide an apparatus and process which modifies the liquid-pervious characteristics of a wide web of material in a plurality of selected relatively narrow zones, and which apparatus can be easily adjusted to change the width of the relatively pervious zone.

Another primary object is to provide a one-piece web which is a multi-component structure including at least one discontinuous fine fiber layer having a melt blown content of greater than 0 but less than 1.5 gsm.

BRIEF DESCRIPTION OF THE INVENTION

In the present inventions process and apparatus is provided for unwinding a pre-formed well-integrated web of woven or nonwoven, hydrophobic or hydrophilic fibers and treating the web to create a coverstock or top sheet for baby diapers or other similar sanitary disposable absorbent products, such as sanitary napkins, adult products and the like. The web is fed across a roll which rotates in a bath of hydrophilic-inducing (or hydrophobic-inducing liquid, depending on whether the web is basically hydrophobic or hydrophilic) to apply the liquid to selected areas of the web. The web then is passed through means for insuring that the web is well impregnated, and through a drying system so as to dry or cure the liquid. The treated web is wound in a roll which is subsequently used on a diaper-making machine. The web, in a preferred embodiment is of a multi-component structure and includes at least one discontinuous fine fiber layer having a melt-blown content of greater than zero but less than 1.5 gsm. This provides for enhanced liquid containment and enhanced liquid transport in a single web.

BRIEF DESCRIPTION OF DRAWINGS

For the purpose of illustrating the invention, the accompanying drawings show a form thereof which is at present preferred, although it is to be understood that the several instrumentalities included in the invention can be variously arranged and organized, and that the invention is not limited to the precise arrangements and organizations of the instrumentalities as herein shown and described.

In the drawings, wherein like reference characters indicate like parts:

FIG. 1 is a schematic diagram of one form of apparatus and process for producing the web of the present invention;

FIG. 2 represents a reproduction of the surface of a hydrophobic web material which has areas treated to render it hydrophilic, showing how the hydrophobic areas repel liquid while the hydrophilic areas permit the liquid to pass through;

FIG. 3 is a schematic diagram, similar to FIG. 1, but showing a preferred apparatus and process of the present invention;

FIG. 4 is a cross-sectional view taken along line 4—4 of FIG. 3;

FIG. 5 is a top plan view of the applicator roll taken generally along line 5—5 of FIG. 3;

FIG. 6 is a view similar to FIG. 4 taken generally along line 6—6 of FIG. 5;

FIG. 7 is a view similar to FIG. 6 taken along line 7—7 of FIG. 5;

FIG. 8 is a perspective view of an applicator roll with a raised liquid-applying portion;

FIG. 9 is a plan view of a baby diaper with a full-length strip of pervious area in the center of the topsheet; and FIG. 10 is a plan view similar to FIG. 9 with an intermittent strip of pervious area in the center of the topsheet.

DETAILED DESCRIPTION OF PRESENTLY PREFERRED EMBODIMENTS

Referring now to FIG. 1, there is shown a preformed, well-integrated roll 20 of nonwoven (or woven) coverstock material W which is unwound in the direction of the arrow 21, turning around a carrier roll 22 so that it can pass between rolls 23 and 24 which comprise a set of press or calender rolls.

Thereafter, the web passes over a first "kiss" or "padding" roll 25 which applies a selected material 26 from a pan or holder 27 when the roll 25 rotates within the material 26 in the direction of the arrow 28. The material may be either a surfactant, such as TRITON X-102 or MAGNASOFT (if the web is hydrophobic in character), or a material such as products Y-12717 made by OSI Specialists of Switzerland, which induce hydrophobicity (if the web is hydrophilic).

If desirable, a second roll 29 can be used, also rotating in a bath 30 of material held within a pan 31 and rotating in the direction of the arrow 32 to apply a second coating. This second coating may be of the same material as applied in the first "kiss" roll or it may be opposite in character and applied in a different area of the web.

Thereafter, the web W passes through a drying chamber 33 and around a turning roll 34 to be rolled up on a winder 35. The winder may be 120 inches wide and may be a combination winder/slitter so that individual rolls of finished coverstock of appropriate width may be produced. Desirable widths presently used in the industry are 15 inches, and on such 15 inch wide webs the central pervious strip may be 5 inches wide with a 5 inch wide strip of impervious material on each side of the central strip.

The application of the material may be continuous so as to provide an uninterrupted treated area (as shown in FIG. 9). This "zebra-like" pattern may be preferred for a variety of reasons, not the least significant of which is ease and economy of operation, even though a small amount of material may be applied in areas where its presence is not critical to the operation of the finished product.

Referring now to FIGS. 3–7 inclusive, there is shown a preferred embodiment of a liquid-applying apparatus of the present invention.

The rolls 60, 61 and 62 replace the rolls 25 and 29 as shown in FIG. 1. The web W moving in the direction of the arrow 63 passes over the top of roll 60 beneath roll 61 and over the top of roll 62.

Roll 60 rotates in the direction of arrow 64, partly submerged in a pan 65 containing the liquid surfactant 66.

As the roll 60 rotates, it picks up on the surface thereof the liquid surfactant which is carried out of the pan 65 and deposited against the web W in the areas C where the web W comes onto contact with the surface of the roll 60. Thus, the applicator roll carries a measured quantity of liquid surfactant onto the web W. As the web passes from roll 60 beneath roll 61 to the top of roll 62 the web is under tension and the pressure of roll 61 against the web W insures migration of the liquid into the web.

The roll 61 is a tensioning roll which keeps the web W stretched between the roll 60 and 62 and tightly against the top of roll 60. The tension can be changed, as desired, by moving the roll 61 up or down in the direction of arrow A. The position of the roll 61 also determines how much surface of rolls 60, 61 and 62 is in contact with the web W, thus also insuring control of the migration of the fluid into the web.

In a preferred embodiment the peripheral speed of the roll 61 may be as much as 10 times greater than the linear speed of the web W, so as to insure that the web is well impregnated with the fluid.

After the impregnated web W passes from the roll 62, it moves into drying chambers 33 as previously described.

As can be seen particularly in FIGS. 3 and 4, at the upstream side 67 of the pan 65, there are supported on the upper edge 68 thereof a plurality of movable covers 69. These covers are mounted on the edge 68 in such a way that they can be moved along the edge 68 in the direction of the arrow 70 shown more particularly in FIGS. 4 and 5.

Each cover 69 has a flexible downstream portion 71 which lies draped on top of the surface of the roll 60 and prevents the liquid surfactant 66 from coming into contact with the web W at those portions where the flexible portion 71 is between the web and the surface of the roll 60 (which has the film of liquid thereon).

In the area C between the covers 71, the web W is pulled into contact with the surface of the roll 60 by the tension which is created in the web by the tensioning roll 61 and thus in those areas C, between the covers 71, the web is impregnated with a liquid.

It is to be easily understood that the covers 71 can be of a specific width and particularly dimensioned so that the uncoated web portions 72 may be as wide as desired, and the placement of the covers 71, by sliding them along the upper edge 68 of the pan portion 67, determines the width of the impregnated portions C between the unimpregnated portions 72.

Thus, as few or as many of the covers may be utilized and they do not all have to be of the same width. Thus, the dimensions of the pervious portion 51 in the final web may be of a dimension as desired by the customer, and the impervious or hydrophobic portions 50 can also be selected to the customer's preference.

Downstream of the dryer member 33, either between the dryer 33 and the turning wheel 34 or between the turning wheel 34 and the windup roll 35, the web may be slit by appropriate slitter knives (not shown) and thus wound up in narrow "doughnut-size" rolls for shipment to the customer.

For the first-mentioned embodiment (shown in FIG. 1) there is used (as shown in FIG. 8), a "kiss" or applicator roll K, (also illustrated at 25 in FIG. 1) which has a raised portion 40 which picks up the material 26 from the carrier pan 27 (or 31). The shape of the raised portion 40 may be chosen to provide the desired area of deposition.

FIG. 10 illustrates how the coating material 56 can be limited to a rectangular area which stops short of the ends of the diaper. This design is easily made by the process and apparatus of FIG. 1.

Although a primary desire is to create a hydrophobic web material treated with a surfactant to render treated areas 51 hydrophilic, it is to be understood that the reverse is just as possible, namely, that the web can be hydrophilic in nature and the treated areas 51 can be rendered hydrophobic.

Particularly useful with the above process of zone coating is to provide a one-piece or unitary web which is of a multi-component structure including at least one discontinuous fine fiber layer (e.g., melt-blown layer) and at least two continuous fiber layers (e.g., spun-bonded layers), wherein the at least one fine fiber layer has a melt blown content of less than 1.5 grams per square meter (gsm), preferably about 0.5 to less than 1.5 gsm. The provision of at least one discontinuous fine fiber layer with the defined melt-blown content serves to enhance both liquid containment and liquid transport within the one-piece web. Thus, zone coating generally, and in particular using the process and apparatus for zone coating as described herein, has been found to be particularly suited to multi-component structures of spun-bonded/melt blown/spun-bonded (SMS) fiber layers and spun-bonded/melt-blown/melt-blown/spun-bonded (SMMS) fiber layers. Zone coating of a wholly spun-bonded layer, however, in particular which is a fine fiber layer with a melt-blown content of less than 1.5 gsm, is also acceptable for use as a liquid absorption and containment product.

A preferred embodiment of a one-piece web having a multi-component integrated structure is a 3-component structure of two outer continuous fiber layers and one or two inner discontinuous fine fiber layers, wherein the inner layer or layers has (have) a melt-blown content of about 0.5 gsm to less than 1.5 gsm. In a further preferred embodiment, this preferred structure includes fibers in each outer layer having a diameter which is a minimum of fifteen percent (15%) larger than the diameter of the fibers of the inner layer or layers. This allows for the use of two carded layers, rather than solely spun-bonded layers, as the outer layers.

The arrangement of the web for the above embodiments can be varied as to the areas which are liquid pervious and liquid impervious. For example, the web may have (1) a liquid pervious center zone continuously bounded along at least a portion of each longitudinally extending edge by a liquid impervious zone, (2) a liquid impervious center zone continuously bounded along at least a portion of each longitudinally extending edge by a liquid pervious zone, (3) a liquid pervious center zone continuously bounded along at least a portion of each longitudinally extending edge by a liquid pervious zone wherein the center zone has a liquid pass-through rate greater than that of the bounding liquid pervious zones, (4) an untreated liquid impervious center zone continuously bounded along at least a portion of each longitudinally extending edge by a liquid pervious zone, (5) an untreated center zone continuously bounded along at least a portion of each longitudinally extending edge by a zone having a hydrostatic pressure greater than that of an untreated zone which is present, and (6) a treated center zone continuously bounded along at least a portion of each longitudinally extending edge by a zone having a hydrostatic pressure less than that of a treated zone which is present.

Thus, the invention also provides the advantage of using a one-piece web as opposed to a two or more-piece web while also providing enhanced liquid containment and liquid transport. Presently, most web manufacturers use two or three individual webs subsequently combined in a conventional manner (e.g., stitching or the like) to provide an optimal combination of absorption and containment. Improved absorption and containment are provided in the present invention when the melt-blown content of the web has a basis weight greater than zero but less than 1.5 gsm regardless of whether the zone coating is provided with a conventional foam or spray head application system or utilizes the zone coating process and apparatus of the present invention. The zone coating process and apparatus of the present invention, however, is preferable in terms of greater improvement in properties obtained as well as economic benefits achieved therewith as described above specifically with respect to the zone coating.

It is to be understood that the present invention may be embodied in other specific forms without departing from the spirit or special attributes hereof, and it is therefore desired that the present embodiments be considered in all respects as illustrative, and therefore not restrictive, reference being made to the appended claims rather than to the foregoing description to indicate the scope of the invention.

It is claimed:

1. A unitary web for use in a disposable article for absorbing and containing liquid, said web comprising selectively treated zones treated to render each zone either liquid pervious or liquid impervious, and said web further comprising one or more integrated component layers with at least one component layer having a melt-blown content greater than zero but less than 1.5 grams per square meter (gsm).

2. The unitary web of claim 1 wherein the melt-blown content is about 0.5 to less than 1.5 gsm.

3. The unitary web of claim 1 wherein said one or more component layers comprise at least one discontinuous fine fiber layer bonded between two continuous fiber layers, and said at least one discontinuous fine fiber layer has a melt-blown content of about 0.5 to less than 1.5 gsm.

4. The unitary web of claim 1 wherein said one or more component layers comprise at least two discontinuous fine fiber layers bonded between two continuous fiber layers, and at least one of said at least two discontinuous fine fiber layers has a melt-blown content of about 0.5 to less than 1.5 gsm.

5. The unitary web of claim 1 wherein said selectively treated zones are provided by contacting a zone to be selectively treated with a patterned area present on a rotating applicator roll containing on said patterned area a liquid material for altering the liquid-pervious character of the zone selectively treated.

6. The unitary web of claim 1 wherein said selectively treated zones are provided by contacting a zone to be selectively treated with a portion of a rotating applicator roll containing on said portion a liquid material for altering the liquid-pervious character of the zone selectively treated, area size of said portion of the applicator roll being defined by placement of at least one cover above said applicator roll and below said web as the web moves over the applicator roll.

7. The unitary web of claim 1 wherein said one or more component layers comprise at least one discontinuous fine fiber layer bonded between two continuous fiber layers, wherein said at least one discontinuous fine fiber layer has a melt blown content of about 0.5 to less than 1.5 gsm, and wherein fibers of said two continuous fiber layers have a diameter which is at least 15% larger than a diameter of fibers in said at least one discontinuous fine fiber layer.

8. The unitary web of claim 1 wherein said selectively treated zones include a liquid pervious center zone continuously bounded on at least a portion of each longitudinally extending edge by a liquid impervious zone.

9. The unitary web of claim 1 wherein said selectively treated zones include a liquid pervious center zone continuously bounded on at least a portion of each longitudinally extending edge by a liquid pervious zone, wherein the center zone has a liquid permeable rate greater than that of each liquid pervious zone bounding the center zone.

10. The unitary web of claim 1 wherein said selectively treated zones include a treated center zone continuously bounded on each longitudinally extending edge by a zone having a hydrostatic pressure less than that of the treated center zone.

11. A unitary web for use in a disposable article for absorbing and containing liquid, said web comprising selectively treated zones treated to render each zone either liquid pervious or liquid impervious, and wherein said selectively treated zones include a liquid impervious center zone continuously bounded on at least a portion of each longitudinally extending edge by a liquid pervious zone; and said web further comprising one or more integrated component layers with at least one component layer having a melt-blown content greater than zero but less than 1.5 grams per square meter (gsm).

12. A unitary web for use in a disposable article for absorbing and containing liquid, said web comprising selectively treated zones treated to render each zone either liquid pervious or liquid impervious, and wherein said selectively treated zones include an untreated liquid impervious center zone continuously bounded on at least a portion of each longitudinally extending edge by a liquid pervious zone; and said web further comprising one or more integrated component layers with at least one component layer having a melt-blown content greater than zero but less than 1.5 grams per square meter (gsm).

13. A unitary web for use in a disposable article for absorbing and containing liquid, said web comprising selectively treated zones treated to render each zone either liquid pervious or liquid impervious, and wherein said selectively treated zones include an untreated center zone continuously bounded on at least a portion of each longitudinally extending edge by a zone having a hydrostatic pressure greater than that of said untreated center zone; and said web further comprising one or more integrated component layers with at least one component layer having a melt-blown content greater than zero but less than 1.5 grams per square meter (gsm).

* * * * *